United States Patent
Breyfogle et al.

(10) Patent No.: US 9,833,391 B2
(45) Date of Patent: Dec. 5, 2017

(54) PERSONAL-CARE COMPOSITION COMPRISING A HYDROCARBON WAX AND A POLAR OIL

(75) Inventors: Laurie Ellen Breyfogle, Milford, OH (US); Paul Robert Tanner, Lebanon, OH (US); Joseph Michael Zukowski, Cincinnati, OH (US)

(73) Assignee: The Proctor & Gamble Company, Cincinnati, OH (US)

( * ) Notice: Subject to any disclaimer, the term of this patent is extended or adjusted under 35 U.S.C. 154(b) by 817 days.

(21) Appl. No.: 12/728,185

(22) Filed: Mar. 19, 2010

(65) Prior Publication Data

US 2011/0020250 A1 Jan. 27, 2011

Related U.S. Application Data

(60) Provisional application No. 61/161,783, filed on Mar. 20, 2009.

(51) Int. Cl.
| | |
|---|---|
| A61K 8/06 | (2006.01) |
| A61K 8/895 | (2006.01) |
| A61K 8/81 | (2006.01) |
| A61Q 17/04 | (2006.01) |
| A61K 8/37 | (2006.01) |
| A61K 8/92 | (2006.01) |
| A61K 8/31 | (2006.01) |

(52) U.S. Cl.
CPC .............. *A61K 8/06* (2013.01); *A61K 8/064* (2013.01); *A61K 8/31* (2013.01); *A61K 8/37* (2013.01); *A61K 8/8111* (2013.01); *A61K 8/895* (2013.01); *A61K 8/92* (2013.01); *A61Q 17/04* (2013.01)

(58) Field of Classification Search
None
See application file for complete search history.

(56) References Cited

U.S. PATENT DOCUMENTS

| | | | |
|---|---|---|---|
| 2,798,053 A | 7/1957 | Brown | |
| 3,755,560 A | 8/1973 | Dickert | |
| 4,206,215 A | 6/1980 | Bailey | |
| 4,421,769 A | 12/1983 | Dixon | |
| 4,509,949 A | 4/1985 | Huang | |
| 4,578,266 A | 3/1986 | Tietjen | |
| 4,980,155 A | 12/1990 | Shah | |
| 5,059,414 A | 10/1991 | Dallal | |
| 5,066,485 A | 11/1991 | Brieva | |
| 5,087,445 A | 2/1992 | Haffey | |
| 5,250,289 A | 10/1993 | Boothroyd | |
| 5,304,334 A | 4/1994 | Lahanas | |
| 5,362,482 A | 11/1994 | Yoneyama | |
| 5,412,004 A | 5/1995 | Tachibana | |
| 5,882,657 A | 3/1999 | Miguel-Colombel | |
| 5,939,082 A | 8/1999 | Oblong | |
| 5,997,887 A | 12/1999 | Ha | |
| 6,015,548 A * | 1/2000 | Siddiqui et al. | 424/59 |
| 6,039,935 A | 3/2000 | Mohammadi | |
| 6,039,960 A | 3/2000 | Chung | |
| 6,177,091 B1 | 1/2001 | Bara | |
| 6,207,596 B1 | 3/2001 | Rourke | |
| 6,235,292 B1 | 5/2001 | Bara | |
| 6,245,344 B1 | 6/2001 | Thibiant | |
| 6,258,345 B1 | 7/2001 | Rouquet | |
| 6,280,753 B1 | 8/2001 | Chung | |
| 6,331,306 B1 | 12/2001 | Afriat | |
| 6,488,941 B1 | 12/2002 | Burnier | |
| 6,492,326 B1 | 12/2002 | Robinson | |
| 6,503,520 B1 * | 1/2003 | Afriat | 424/401 |
| 6,503,944 B1 | 1/2003 | Chanchani | |
| 6,524,598 B2 | 2/2003 | Sunkel | |
| 6,544,532 B1 | 4/2003 | Jager-Lezer | |
| 6,548,050 B1 | 4/2003 | Bara | |
| 6,696,049 B2 | 2/2004 | Vatter | |
| 6,905,695 B1 | 6/2005 | Afriat | |
| 6,949,504 B2 * | 9/2005 | Mondet et al. | 514/1 |
| 7,001,592 B1 * | 2/2006 | Traynor et al. | 424/59 |
| 7,179,880 B2 * | 2/2007 | Kawa et al. | 528/196 |
| 2002/0037302 A1 | 3/2002 | Afriat | |
| 2003/0082219 A1 | 5/2003 | Warren | |
| 2003/0082222 A1 * | 5/2003 | Miyamoto | 424/401 |
| 2004/0175347 A1 | 9/2004 | Bissett | |
| 2004/0176273 A1 | 9/2004 | Bissett | |
| 2004/0219124 A1 | 11/2004 | Gupta | |
| 2004/0223989 A1 * | 11/2004 | Auguste et al. | 424/401 |

(Continued)

FOREIGN PATENT DOCUMENTS

| | | |
|---|---|---|
| EP | 374332 B1 | 1/1993 |
| EP | 1044672 A1 | 10/2000 |

(Continued)

OTHER PUBLICATIONS

Leotsakos "Wax-based slip and mar additives" in Handbook of Coating Additives Ed. Florio et al. Marcel Dekker Inc.:New York 2004 p. 235 and 239.*

(Continued)

*Primary Examiner* — Robert A Wax
*Assistant Examiner* — Caralynne Helm
(74) *Attorney, Agent, or Firm* — John G. Powell; S. Robert Chuey; Eric T. Addington

(57) ABSTRACT

In one embodiment, a stable personal-care composition in the form of a water-in-oil emulsion may comprise a hydrocarbon wax, a polar oil, and a non-emulsifying silicone elastomer. In another embodiment, a stable personal-care composition in the form of a water-in-oil emulsion may comprise a hydrocarbon wax and a polar oil. The weight ratio of the hydrocarbon wax to the polar oil is from about 0.01 to about 0.5. The personal-care composition allows for previously unattainable levels of polar oils and/or aqueous phase within a water-in-oil emulsion.

13 Claims, No Drawings

(56) References Cited

U.S. PATENT DOCUMENTS

| | | |
|---|---|---|
| 2004/0228884 A1 | 11/2004 | Gupta |
| 2004/0234477 A1 | 11/2004 | Sakuta |
| 2005/0019356 A1 | 1/2005 | Bissett |
| 2005/0136012 A1 | 6/2005 | Gonzalez |
| 2005/0142079 A1 | 6/2005 | Garrison |
| 2005/0191329 A1 | 9/2005 | Taniguchi |
| 2005/0220728 A1* | 10/2005 | Kanji et al. ............ 424/59 |
| 2006/0013792 A1* | 1/2006 | Fontaine et al. ........ 424/70.12 |
| 2006/0013793 A1 | 1/2006 | Themens |
| 2006/0074097 A1 | 4/2006 | Bissett |
| 2006/0141078 A1* | 6/2006 | Guillou et al. ............ 424/750 |
| 2006/0147508 A1 | 7/2006 | Gupta |
| 2006/0193807 A1* | 8/2006 | Lezer et al. ............ 424/70.13 |
| 2006/0263309 A1 | 11/2006 | Bissett |
| 2006/0275237 A1 | 12/2006 | Bissett |
| 2007/0009453 A1* | 1/2007 | Willemin et al. ........... 424/59 |
| 2007/0128137 A1 | 6/2007 | Yoshimi |
| 2007/0196400 A1 | 8/2007 | Raschke |
| 2007/0248550 A1 | 10/2007 | Patel |
| 2007/0264210 A1 | 11/2007 | Robinson |
| 2007/0274932 A1 | 11/2007 | Suginaka |
| 2007/0297996 A1 | 12/2007 | Tanner |
| 2007/0297997 A1 | 12/2007 | Tanner |
| 2008/0038216 A1 | 2/2008 | Zukowski |
| 2008/0038360 A1 | 2/2008 | Zukowski |
| 2009/0003920 A1 | 1/2009 | Zukowski |
| 2009/0011035 A1 | 1/2009 | Zukowski |
| 2009/0257966 A1* | 10/2009 | Schlossman et al. ........ 424/59 |
| 2009/0298971 A1* | 12/2009 | Leotsakos et al. ......... 523/207 |
| 2010/0092408 A1 | 4/2010 | Breyfogle |
| 2010/0119619 A1 | 5/2010 | Griffiths-Brophy |
| 2010/0135918 A1* | 6/2010 | Kim et al. ............... 424/47 |
| 2010/0158824 A1 | 6/2010 | Lin |
| 2010/0172849 A1 | 7/2010 | Shaow |
| 2010/0183525 A1 | 7/2010 | Lin |
| 2010/0303744 A1 | 12/2010 | Breyfogle |
| 2010/0305168 A1 | 12/2010 | Robinson |
| 2010/0305169 A1 | 12/2010 | Robinson |
| 2011/0212144 A1* | 9/2011 | Lemoine et al. ........... 424/401 |
| 2012/0003284 A1* | 1/2012 | Arnaud et al. ............. 424/401 |

FOREIGN PATENT DOCUMENTS

| | | |
|---|---|---|
| EP | 1166746 B1 | 7/2003 |
| EP | 1068851 B1 | 9/2004 |
| EP | 1068852 B1 | 9/2004 |
| EP | 1466586 | 10/2004 |
| EP | 1003460 B1 | 7/2005 |
| EP | 1473016 | 11/2006 |
| JP | 53148545 | 12/1978 |
| JP | 2000355520 | 4/1994 |
| JP | 10273433 A | 10/1998 |
| JP | 200086484 A1 | 3/2000 |
| JP | 2000-191442 A | 7/2000 |
| JP | 2001187711 | 7/2001 |
| JP | 2003055141 | 2/2003 |
| JP | 2003212747 | 7/2003 |
| JP | 2005-112770 A | 4/2005 |
| JP | 2005272469 | 10/2005 |
| JP | 2007503417 | 2/2007 |
| JP | 2007523198 | 8/2007 |
| JP | 2008163018 | 7/2008 |
| WO | WO2004078157 | 9/2004 |
| WO | WO 2007017434 A1 * | 2/2007 |
| WO | 2007086022 A2 | 8/2007 |
| WO | WO2007109282 | 5/2008 |

OTHER PUBLICATIONS

Product Data Sheet of "Accumelt 90", International Group Inc., Toronto, Ontario, 2013.

* cited by examiner

PERSONAL-CARE COMPOSITION COMPRISING A HYDROCARBON WAX AND A POLAR OIL

CROSS REFERENCE TO RELATED APPLICATION

This application claims the benefit of Provisional Application Ser. No. 61/161,783, filed Mar. 20, 2009.

FIELD OF THE INVENTION

The present invention relates to a personal-care composition in the form of a water-in-oil emulsion comprising a hydrocarbon wax, a polar oil, and a non-emulsifying silicone elastomer.

BACKGROUND OF THE INVENTION

An ongoing need exists to provide personal-care compositions that prevent damage to the skin and other keratinous tissue from harmful ultraviolet radiation (UV). Much attention has been directed to improving the UV blocking efficacy of personal-care compositions. Most of this work is focused on improving the efficacy and stability of the sunscreen actives within the compositions. While this work has resulted in significant improvements in protection, there are other factors that impact the UV blocking efficacy of personal-care compositions. To provide adequate protection, these personal-care compositions must be applied regularly and in a requisite amount. Therefore, a need exists for personal-care compositions that encourage frequent and ample use, such as by having a pleasant feel without being oily or unstable.

The majority of highly effective sunscreens are oily or oil-soluble. These sunscreens are necessary for UV blocking, but have an unpleasant heavy, oily skin feel and present formulation difficulties such as product stability and compatibility with other components. To counter the heavy, oily skin feel associated with sunscreen compositions, such products are commonly formulated as emulsions. The majority of such emulsions are oil-in-water emulsions wherein the aqueous phase (which in most cases is predominantly water) is thickened with polymeric thickeners. Considerably fewer sunscreen compositions in the form of an inverse emulsion (water-in-oil) exist. Inverse emulsions have a tendency to feel greasy and heavy when the external phase is built using a traditional gel network structure comprising, e.g., mineral oil and fatty alcohols. Alternatively, if silicone-based materials are selected as the primary oil-phase components, other issues become critical, including sunscreen solubility and product stability. It is challenging to thicken the oil-continuous phase with commercially-available materials and still provide consumer-required skin feel.

One way to thicken the composition and provide better skin feel is to use silicone elastomers. However, silicone elastomers are expensive and inefficient. Silicone elastomers typically collapse in the presence of polar sunscreen oils, which ultimately results in product instability in the form of syneresis. This destabilization imposes limits on the amount of polar oil that may be included within the product. In cases where the polar oil is a sunscreen, the product may then have reduced or limited UV protection benefits. There is a desire to develop a structured chassis so that even at high concentrations of polar oil, syneresis does not occur in water-in-oil emulsions.

While it may be possible to thicken and stabilize the oil phase using various types of waxy materials, the resulting emulsions are often aesthetically disadvantageous and/or unstable at higher temperatures. Typically water-in-oil emulsions formulated with wax are solids at room temperature. Consumers find it aesthetically undesirable to use a solid stick on the face and neck. Additionally, at high temperatures, a significant portion of the wax may melt, leading to changes in product viscosity/rheology that compromise the product's composition or aesthetic properties—for example, syneresis, component settling, or substantial viscosity growth.

Therefore, a need exists for a personal-care composition in the form of a water-in-oil emulsion providing ample UV protection and the desirable skin feel attributes of silicone elastomers while maintaining suitable viscosity and stability.

SUMMARY OF THE INVENTION

In one embodiment, the present invention relates to a stable personal-care composition in the form of a water-in-oil emulsion comprising a hydrocarbon wax, a polar oil, and a non-emulsifying silicone elastomer. Personal-care compositions with hydrocarbon wax exhibit increased stability and provide greater flexibility in formulation. This unexpected stability advantage allows for the formation of water-in-oil emulsions with high levels of consumer beneficial components. In certain embodiments, the water-in-oil emulsions may comprise high levels of polar oil, high levels of water, or high levels of both. As will be seen in the Comparative Examples, the high levels of polar oil and/or aqueous phase were previously unachievable or undesirable with conventional materials and methods.

In one embodiment, the present invention relates to a stable personal-care composition in the form of a water-in-oil emulsion comprising from about 0.01% to about 10% of a hydrocarbon wax; greater than about 10% of a polar oil; and from about 1% to about 8% of a non-emulsifying silicone elastomer; wherein the weight ratio of wax to polar oil is from about 0.01 to about 0.5.

In another embodiment, the present invention relates to a stable personal-care composition in the form of a water-in-oil emulsion comprising from about 0.01% to about 10% of a hydrocarbon wax and greater than about 10% of a polar oil; wherein the weight ratio of wax to polar oil is from about 0.1 to about 0.5.

In another embodiment, the present invention relates to a stable personal-care composition in the form of a water-in-oil emulsion comprising from about 4% to about 6% of a hydrocarbon wax; greater than about 20% of a polar oil; from about 5% to about 7% of a non-emulsifying silicone elastomer; and a skin-care active selected from the group consisting of a vitamin $B_3$ compound, a sugar amine, a peptide, a hexamidine compound, and combinations thereof; wherein the weight ratio of wax to polar oil is from about 0.1 to about 0.3.

In another embodiment, the present invention relates to a method for improving the stabilization of polar oils in a water-in-oil emulsion, comprising the step of preparing a stable personal-care composition comprising from about 0.01% to about 10% of a hydrocarbon wax, greater than about 10% of a polar oil, and from about 1% to about 8% of a non-emulsifying silicone elastomer, wherein the weight ratio of wax to polar oil is from about 0.01 to about 0.5.

DETAILED DESCRIPTION OF THE INVENTION

All percentages are by weight of the personal-care composition, unless otherwise specified. All ratios are weight ratios, unless specifically stated otherwise. All numeric ranges are inclusive of narrower ranges; delineated upper and lower range limits are interchangeable to create further ranges not explicitly delineated. The number of significant digits conveys neither limitation on the indicated amounts nor on the accuracy of the measurements. All measurements are understood to be made at about 25° C. and at ambient conditions, where "ambient conditions" means conditions under about one atmosphere of pressure and at about 50% relative humidity.

"Personal-care composition," as used herein, means compositions suitable for topical application on mammalian keratinous tissue. Compositions of the present invention may be used in skin-care, cosmetic, and hair-care products; non-limiting uses of which include antiperspirants, deodorants, lotions (e.g. hand lotion and body lotion), skin-care products (e.g., face and neck lotions, serums, sprays), sunless tanners, cosmetics (e.g., foundation, concealer, blush, lipstick, lip gloss), depilatories, shampoos, conditioning shampoos, hair conditioners, hair dyes, body washes, moisturizing body washes, shower gels, skin cleansers, cleansing milks, hair and body washes, in-shower body moisturizers, pet shampoos, shaving preparations, after-shaves, razor moisturizing/lubricating strips, razor shave-gel bars, bar soaps, cleansing products, feminine-care products, oral-care products, and baby-care products. The methods of using any of the aforementioned compositions are also included within the meaning of personal-care composition.

"Keratinous tissue," as used herein, refers to keratin-containing layers disposed as the outermost protective covering of mammals which includes, but is not limited to, skin, hair, and nails.

"Stable" and "stability," as used herein, refer to compositions which are substantially unaltered in chemical state, physical homogeneity and/or color, upon exposure to conditions reasonably expected to be incurred in shipping, storage and use, for example, for at least 30 days at a temperature of from about 0° C. to about 40° C.

"Derivatives," as used herein, means ester, ether, amide and/or salt derivatives of the relevant compound.

"Polar," as used herein, means a material with a solubility parameter of greater than or equal to 7.4 (calories/cm$^3$)$^{0.5}$ to about 11 (calories/cm$^3$)$^{0.5}$. "Non-polar," as used herein, means a material with a solubility parameter of less than 7.4 (calories/cm$^3$)$^{0.5}$. Solubility parameters are discussed in more detail by C. D. Vaughan in "The Solubility Parameter: What is it?," Cosmetics & Toiletries vol. 106, November, 1991, pp. 69-72. Solubility parameter may be determined or calculated according to procedures discussed within Barton, AFM (1991), *Handbook of Solubility Parameters and Other Cohesion Parameters*, 2nd edition, CRC Press.

As discussed in the Background, containment of polar oils in a water-in-oil emulsion is challenging, especially as the level of polar oil is increased in an effort to deliver higher SPF protection. Such compositions tend to exhibit instability in the form of syneresis. To compensate for the instability, previous approaches included using wax to create a solid stick thereby trapping the oils or using a high level of expensive and inefficient silicone elastomer to thicken and support the external phase. Both approaches have drawbacks in terms of the overall formulation flexibility (e.g., limits to polar oil capacity, water phase volume, etc.) and skin feel aesthetics.

To overcome the challenge of stabilizing moderate to high levels of polar oil in a water-in-oil emulsion and maintain formulation flexibility, we found that inclusion of specific hydrocarbon waxes leads to unexpected and significant enhancements in stability. Unlike solid products which contain a wax crystal network to trap the oil, the stability advantage obtained with these hydrocarbon waxes holds regardless of the degree of connections between crystals, i.e. a crystal network is not necessary to contain the oil. Discrete wax crystals within the oil phase provide the stability benefit and flexibility to create lotions and creams. This finding greatly expands the aesthetics of the range of stable products from a solid to a cream to a lotion.

This stability advantage is only observed with specific waxes—hydrocarbon waxes, especially those that are saturated and straight-chains. Waxes outside this category either do not prevent syneresis, or are subject to a second type of product instability—an increase in viscosity at warm temperatures. This undesirable, uncontrolled increase in viscosity changes the product performance and aesthetics. Accordingly, the presence of a hydrocarbon wax in the oil phase greatly enhances the formulation flexibility of water-in-oil emulsions comprising sunscreen polar oils. In addition to selecting the proper wax, to obtain the stability advantage and aesthetic benefits, the wax to polar oil ratio should be kept within a specific range.

I. Personal-Care Composition

The personal-care composition of the present invention is a water-in-oil emulsion. The personal-care composition may have a viscosity of from about 5,000 cps (centipoise) to about 1,000,000 cps, alternatively from about 10,000 cps to about 500,000 cps, and alternatively from about 15,000 cps to about 200,000 cps.

In one embodiment, the personal-care composition may comprise at least about 5% of an aqueous phase. A unique aspect of the personal-care composition is that greater loading of the aqueous phase can be obtained while still providing ample formulation space for other ingredients such as polar oils and silicones. In certain embodiments, the personal-care composition may comprise from about 5% to about 50% of an aqueous phase, or from about 10% to about 25% of an aqueous phase. Within the emulsion the aqueous phase is the internal or discontinuous phase.

The aqueous phase typically comprises water. The aqueous phase may be comprised entirely of water. In other embodiments, the aqueous phase may comprise components other than water (i.e., non-water components), including but not limited to water-soluble moisturizing agents, conditioning agents, anti-microbials, humectants and/or other water-soluble skin care actives, to impart an increased benefit to the keratinous tissue. In one embodiment, the aqueous phase of the personal-care composition comprises a humectant such as glycerin and/or other polyols. The aqueous phase may be substantially to totally free of water.

In one embodiment, the personal-care composition may comprise at least about 15% of an oil phase. In certain embodiments, the personal-care composition comprises from about 20% to about 90% of an oil phase, or from about 40% to about 90% of an oil phase. Within the emulsion, the oil phase is the external or continuous phase. The oil phase may comprise silicone oils, non-silicone oils such as hydrocarbon oils, esters, ethers, the like, and mixtures thereof. In a one embodiment, the oil phase comprises silicone oils, polar hydrocarbon oils, and mixtures thereof.

A. Polar Oil

In one aspect, the composition comprises a polar oil. In some embodiments, the composition may comprise greater than about 10% of polar oil. In other embodiments, the composition may comprise greater than about 20% of polar oil. In certain embodiments, the polar oil may have a solubility parameter of from about 7.4 $(calories/cm^3)^{0.5}$ to about 11 $(calories/cm^3)^{0.5}$.

Suitable polar oils include ethers, esters, amides, propoxylates, and mixtures thereof. The aforementioned oils may be saturated, unsaturated, aliphatic (straight or branched chains), alicyclic, or aromatic.

Suitable polar oils include but are not limited to, butyl and isopropyl phthalimide (Pelemol™ BIP), phenylethyl benzoate (X-tend™ 226), dicaprylyl carbonate (Tegosoft™ DEC), isopropyl lauroyl sarcosinate (Eldew™ SL 205), butyl octylsalicylate (Hallbrite™ BHB), dioctyl malate, dicaprylyl maleate (Hallbrite™ DCM), di-isopropyl adipate, dibutyl adipate (Cetiol B), isononyl isononanoate, isopropyl isostearate, propylene glycol dicaprate, C12-15 alcohol benzoate (Finsolv TN), PPG-11 stearyl ether, and derivatives and mixtures thereof.

Other exemplary polar oils include retinoid such as retinol and retinol propionate, tocopherol (i.e., vitamin E), derivatives of tocopherol, and tetrahexyldecyl ascorbate.

Sunscreens are another example of polar oils. Exemplary sunscreens include but are not limited to, benzophenone-3, bis-ethylhexyloxyphenol methoxyphenyl triazine, butyl methoxydibenzoylmethane, diethylamino hydroxy-benzoyl hexyl benzoate, ethylhexyl triazone, drometrizole trisiloxane, ethylhexyl methoxy-cinnamate, ethylhexyl salicylate, octocrylene, homosalate, polysilicone-15, 2-ethylhexyl N,N-dimethyl-p-aminobenzoate, 4-isopropyl dibenzoylmethane, 3-(4-methylbenzylidene) camphor, 3-benzylidene camphor, and menthyl anthranilate. In one embodiment, the composition comprises more than one sunscreen.

In one embodiment, the polar oil comprises at least one oil-soluble sunscreen which, in its commercially-available purified form, is an oil-soluble crystalline and/or solid compound. It is to be understood that the oil-soluble crystalline and/or solid sunscreen is substantially dissolved, and thus does not remain in a crystalline form in the personal-care composition of the present invention. For example, a suitable polar oil may comprise a combination of an oil-soluble crystalline sunscreen and a solvent such as butyl methoxydibenzoylmethane with isopropyl lauroyl sarcosinate. Particularly suitable crystalline sunscreens include benzophenone-3, bis-ethylhexyloxyphenol methoxyphenyl triazine, butyl methoxydibenzoylmethane, diethylamino hydroxy-benzoyl hexyl benzoate, and ethylhexyl triazone.

B. Hydrocarbon Wax

In one aspect, the composition comprises a hydrocarbon wax. "Hydrocarbon wax," as used herein, means a substance that is solid at room temperature and consists of the elements carbon and hydrogen. The hydrocarbon wax is substantially free of heteroatoms (i.e. oxygen, nitrogen), as it is made from pure hydrocarbon reactants. Any heteroatom present in the hydrocarbon wax is an unintended impurity. The hydrocarbon structure may be straight, branched, or napthenic and may be derived synthetically or naturally. Sources include, but are not limited to, Fischer-Tropsch synthesis, alkene polymerization, petrolatum, and mineral. In certain embodiments, the personal-care composition comprises from about 0.01% to about 10%, or from about 1% to about 8%, or from about 4% to about 6%, by weight of the composition, of a hydrocarbon wax.

Suitable hydrocarbon waxes include saturated hydrocarbons. In one embodiment, straight-chain hydrocarbon waxes, as defined by having an alkyne:alkene carbon ratio lower than about 0.05, are preferred. Examples include, but are not limited to, polyethylene, polymethylene, and similar synthetic waxes. In some embodiments, the composition comprises more than one type of hydrocarbon wax.

In certain embodiments, the hydrocarbon wax may exhibit one or more of the following: a saturation of greater than about 90%; from 20 to 100 carbon atoms, or from 25 to 80 carbon atoms, or from 30 to 70 carbon atoms; an alkyne:alkene carbon ratio lower than about 0.05; a breadth of molecular weight distribution or polydispersity index of less than about 1.1, or less than about 1.05, as defined by the weight-average degree of polymerization divided by the number-average degree of polymerization; a melt point of from about 55 degrees C. to about 150 degrees C., or from about 65 degrees C. to about 100 degrees C.; a needle penetration at 25 degrees C. as measured by ASTM 1321 of from about 1 dmm to about 45 dmm, or from about 2 dmm to about 15 dmm, or from about 2 dmm to about 10 dmm. The unit dmm designates tenths of a millimeter.

It has been found that if the weight ratio of wax to polar oil is too low, the composition becomes unstable and synereses. Conversely, if the weight ratio of wax to polar oil is too high, the composition takes the form of a solid stick. A variety of waxes were previously used to stabilize oils and/or emulsions by creating solid sticks. "Solid," as used herein, means a composition with a harness of greater than or equal to 0.12 newtons (N) as measured by a texture analyzer. Hardness is the force in N necessary for a cylindrical probe having a diameter of 2 mm to penetrate a distance of 0.5 mm at a rate of 0.1 mm/s into the composition, using a TA-XT2i Texture Analyzer with Texture Expert Exceed software (v. 2.64). Prior to measuring the hardness, the composition is allowed to equilibrate to 25±1 degrees C. In solid sticks, a continuous wax network forms thereby entrapping the oil. However, solid sticks are unappealing to consumers. Solid sticks feel noticeably waxy—e.g., heavy, less powdery soft, and slow absorbing. These negative aesthetics are particularly noticeable and highly undesirable when applied to the face and neck. These negative aesthetics are particularly noticeable and undesirable when applied to the face and neck. Accordingly, it has been found that a weight ratio of wax to polar oil of from about 0.01 to about 0.5, or from about 0.1 to about 0.5, or from about 0.1 to about 0.3 is suitable.

C. Non-Emulsifying Silicone Elastomer

In one aspect, the composition comprises a non-emulsifying silicone elastomer. "Non-emulsifying silicone elastomer" means that the silicone elastomer comprises no polyoxyalkylene groups. The personal-care composition may comprise from about 1% to about 8%, or from about 2% to about 8%, or from about 3% to about 7%, by weight of the composition, of a non-emulsifying silicone elastomer.

Suitable non-emulsifying silicone elastomers include the CTFA (Cosmetic, Toiletry, and Fragrance Association *International Cosmetic Ingredient Dictionary and Handbook*, 11th ed.) designated dimethicone/vinyl dimethicone crosspolymers such as supplied by Dow Corning™ (DC 9506), General Electric™ (SFE 839), Shin Etsu™ (KSG 15 and 16), and Grant Industries (GRANSIL™ RPS-NA) and dimethicone/phenyl vinyl dimethicone crosspolymer such as KSG 18 available from Shin Etsu™. Other exemplary silicone elastomers include the CTFA designated dimethicone crosspolymers including Dow Corning™ (DC 9040, DC 9041, DC 9045). It should be recognized that non-emulsifying silicone elastomers may be supplied pre-swollen with a solvent. With a pre-swollen elastomer, the weight percentages recited above are of the elastomer particles alone (excluding the weight of the solvent).

The non-emulsifying silicone elastomer provides structuring in addition to that provided by the hydrocarbon wax, but is not required for product stability. In one embodiment, the composition is free of elastomer. Even without the non-emulsifying elastomer, the product is stable against oil syneresis at room temperature and up to 50 degrees C.

While non-emulsifying silicone elastomer structures may be used to structure water-in-oil emulsions containing lower levels of polar oil, they are not very efficient structurants. Because of their inefficiency, large volumes of relatively expensive non-emulsifying silicone elastomers are required to even hold low levels of polar oil. This is restrictive in both the level of SPF protection attainable and the remaining capacity for additional ingredients. This limits the overall flexibility of the water-in-oil formulation comprising polar oil.

D. Emulsifier

In one aspect, the composition comprises one or more emulsifiers that may be linear, branched, and/or cross-linked. In certain embodiments, the personal-care composition may comprise from about 0.05% to about 20%, or from about 0.1% to about 10%, by weight of the composition, of total emulsifier. Non-limiting examples of emulsifiers are disclosed in U.S. Pat. Nos. 3,755,560, 4,421,769, and *McCutcheon's Detergents and Emulsifiers*, North American Edition and International Edition, pages 235-246 (1993).

Emulsifiers may include emulsifying silicone elastomers. Suitable emulsifying silicone elastomers include cross-linked organopolysiloxane elastomers having at least one polyalkyl ether unit. These cross-linked elastomers may also be co-modified to include alkyl substituents. Particularly useful emulsifying polyoxyethylene cross-linked elastomers include Shin Etsu's KSG-21, KSG-210, KSG-24, KSG-240, KSG-31, KSG-310, KSG-32, KSG-320, KSG-33, KSG-330, KSG-34, and KSG-340.

Linear or branched type silicone emulsifiers are also useful in this application. Particularly useful polyether or polyglycerolated modified silicone emulsifiers include Shin Etsu's KF-6100, KF-6104, KF-6105, KF-6011, KF-6012, KF-6013, KF-6015, KF-6016, KF-6017, KF-6043, KF-6028, and KF-6038.

Emulsifiers are necessary, but not sufficient for stabilization of water-in-oil emulsions which comprise polar oils. Without the support of sufficient structurants, the emulsion quickly syneresis.

II. Optional Ingredients

A. Particulate Material

In particular embodiments, the composition comprises from about 0.1% to about 40%, or from about 1% to about 30%, or from about 5% to about 20%, by weight of the composition, of one or more particulate materials. Non-limiting examples of suitable powders include inorganic powders (for example, iron oxides, titanium dioxides, zinc oxides, silica), organic powders, composite powders, optical brightener particles, and mixtures of any of the foregoing. These particulates can, for instance, be platelet shaped, spherical, elongated or needle-shaped, or irregularly shaped; surface coated or uncoated; porous or non-porous; charged or uncharged; and can be added to the current compositions as a powder or as a pre-dispersion. In one embodiment, the particulate material is hydrophobically coated.

Suitable organic powder particulate materials include, but are not limited, to polymeric particles chosen from the methylsilsesquioxane resin microspheres, e.g., Tospearl™ 145A, (Toshiba Silicone); microspheres of polymethylmethacrylates, e.g., Micropearl™ M 100 (Seppic); the spherical particles of crosslinked polydimethylsiloxanes, e.g., Trefil™ E 506C or Trefil™ E 505C (Dow Corning Toray Silicone); spherical particles of polyamide, e.g., nylon-12, and Orgasol™ 2002D Nat C05 (Atochem); polystyrene microspheres, e.g., Dyno Particles, sold under the name Dynospheres™, and ethylene acrylate copolymer, sold under the name FloBead™ EA209 (Kobo); aluminum starch octenylsuccinate, e.g., Dry Flo™ (National Starch); polyethylene particulates, e.g., Microthene™ FN510-00 (Equistar) and Micropoly° 220L (Micro Powders, Inc.); microspheres of polypropylene, e.g., Mattewax™ 511 (Micro Powders, Inc.); silicone resin; polymethylsilsesquioxane silicone polymer; platelet shaped powder made from L-lauroyl lysine; and mixtures thereof.

In particular embodiments, the composition comprises interference pigments, including hydrophobically-modified interference pigments. Herein, "interference pigments" means thin, plate-like layered particles having two or more layers of controlled thickness. The layers have different refractive indices that yield a characteristic reflected color from the interference of typically two, but occasionally more, light reflections, from different layers of the plate-like particle. One example of interference pigments are micas layered with about 50-300 nm films of $TiO_2$, $Fe_2O_3$, silica, tin oxide, and/or $Cr_2O_3$ and include pearlescent pigments. Interference pigments are available commercially from a wide variety of suppliers, for example, Rona (Timiron™ and Dichrona™), Presperse (Flonac™), Englehard (Duochrome™), Kobo (Interfine, Interval, SK-45-R, and SK-45-G), BASF (Sicopearls™) and Eckart (Prestige™). In one embodiment, the average diameter of the longest side of the individual particles of interference pigments is less than about 75 microns, and alternatively less than about 50 microns.

Particulates may also include colorants. Non-limiting examples of suitable colorants include iron oxides, ferric ammonium ferrocyanide, manganese violet, ultramarine blue, and chromium oxide, phthalocyanine blue and green pigment, encapsulated dyes, inorganic white pigments, for example $TiO_2$, ZnO, or $ZrO_2$, FD&C dyes, D&C dyes, and mixtures thereof.

B. Insoluble Sunscreens

In particular embodiments, the composition comprises from about 0.001% to about 10%, or from about 0.1% to about 5%, by weight of the composition, of an insoluble sunscreen. Non-limiting examples of suitable insoluble sunscreens include methylene bis-benzotriazolyl tetramethyl-butyl-phenol (Tinosorb M), titanium dioxides, zinc cerium oxides, zinc oxides, and derivatives and mixtures thereof.

C. Skin Care Actives

In particular embodiments, the composition comprises one or more skin care actives. Suitable skin care actives include, but are not limited to, vitamins, peptides, sugar amines, sunscreens, oil control agents, tanning actives, anti-acne actives, desquamation actives, anti-cellulite actives, chelating agents, skin lightening agents, flavonoids, protease inhibitors, non-vitamin antioxidants and radical scavengers, hair growth regulators, anti-wrinkle actives, anti-atrophy actives, minerals, phytosterols and/or plant hormones, tyrosinase inhibitors, anti-inflammatory agents, N-acyl amino acid compounds, antimicrobials, and antifungals. These skin care actives and others are provided in further detail in U.S. Application Publication Nos. US2006/0275237A1, US2004/0175347A1, and US2006/0263309A1.

Particularly suitable skin actives include a vitamin $B_3$ compound, a sugar amine, a peptide, a hexamidine compound, and combinations thereof. As used herein, "vitamin $B_3$ compound" means a compound having the formula:

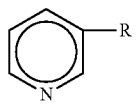

wherein R is —CONH$_2$ (i.e., niacinamide), —COOH (i.e., nicotinic acid) or —CH$_2$OH (i.e., nicotinyl alcohol); derivatives thereof; and salts of any of the foregoing. As used herein, "sugar amine" includes isomers and tautomers of such and its salts (e.g., HCl salt) and its derivatives. Examples of sugar amines include glucosamine, N-acetyl glucosamine, mannosamine, N-acetyl mannosamine, galactosamine, N-acetyl galactosamine, their isomers (e.g., stereoisomers), and their salts (e.g., HCl salt). As used herein, "peptide" refers to peptides containing ten or fewer amino acids and their derivatives, isomers, and complexes with other species such as metal ions (e.g., copper, zinc, manganese, magnesium, and the like). As used herein, "hexamidine compound" means a compound having the formula:

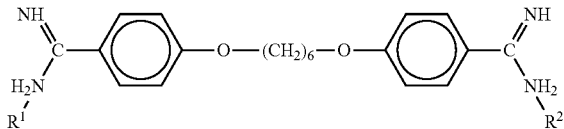

wherein R$^1$ and R$^2$ are optional or are organic acids (e.g., sulfonic acids, etc.), and its salts and derivatives.

Further suitable skin care actives include white tea extract, green tea extract, ginseng, and other natural or botanical compounds.

D. Non-Polar Emollient

In particular embodiments, the composition comprises from about 10% to about 70%, and alternatively 30% to about 50% of a non-polar emollient. Non-limiting examples of suitable non-polar emollients include silicone oils, hydrocarbon oils, and mixtures thereof. Useful non-polar emollients in the present invention include natural, synthetic, saturated, unsaturated, straight chained, branched chained, linear, cyclic, aromatic, volatile, and non-volatile non-polar emollients, and mixtures thereof.

Non-limiting examples of suitable non-polar hydrocarbon oils include mineral oils and branched chain hydrocarbons (such as commercially available, for example, under the tradenames Permethyl™ (Permethyl Corporation™) and Isopar™ (Exxon™)). Non-limiting examples of suitable non-polar silicone oils include linear and cyclic polydimethylsiloxanes, including cyclomethicones (cyclotetrasiloxane, cyclopentasiloxane, cyclohexasiloxane), dimethicones, and mixtures thereof. Commercially available examples of these types of silicones include the Dow Corning 200 series, Dow Corning 344, and Dow Corning 345 (all available from Dow Corning™ Corp.); and SF1202, SF1204, and the Viscasil™ series (all available from the G.E. Silicones™). Additional non-polar silicone oils include alkyl (for example, 2 carbons to 30 carbons) and aryl (for example, phenyl or styrenyl) substituted silicones, including by not limited to phenyl methicone, phenyl dimethicone, phenyl trimethicone, diphenyl dimethicone, phenylethyl dimethicone, hexyl dimethicone, lauryl dimethicone, cetyl dimethicone, stearyl dimethicone, bis-stearyl dimethicone, and mixtures thereof. In one embodiment, the non-polar emollient is low viscosity, meaning a viscosity less than 50 cst.

With the non-polar emollients in the external phase of the water-in-oil emulsion, it is difficult to prevent syneresis without sufficient structurants.

III. Methods

The present invention further relates to a method of improving the stability of water-in-oil emulsions comprising polar oils. One embodiment is directed to a method for improving the stability of water-in-oil emulsions comprising polar oils comprises the step of preparing a stable personal-care composition comprising from about 0.01% to about 10% of a hydrocarbon wax, greater than about 10% of a polar oil, and from about 1% to about 8% of a non-emulsifying silicone elastomer, wherein the weight ratio of wax to polar oil is from about 0.01 to about 0.5. This method allows for previously unattainable levels of polar oils and/or aqueous phase within a water-in-oil emulsion.

The present invention further relates to methods of protecting keratinous tissue from the harmful effects of UV radiation. Such methods generally involve attenuating or reducing the amount of UV radiation which reaches the keratinous tissue. In certain embodiments, the personal-care compositions described herein are suitable for use as a sunscreen to provide protection to keratinous tissue from the harmful effects of UV radiation such as sunburn, dry or damaged hair, and premature aging of the skin.

In a further aspect, the personal-care compositions may be used to improve or regulate the condition of keratinous tissue. Conditions to be improved or regulated include increasing the luminosity or "glow" of the skin, reducing the appearance of wrinkles and coarse deep lines, fine lines, crevices, bumps, and large pores; thickening of keratinous tissue (e.g., building the epidermis and/or dermis and/or sub-dermal layers of the skin, and where applicable the keratinous layers of the nail and hair shaft, to reduce skin, hair, or nail atrophy); increasing the convolution of the dermal-epidermal border (also known as the rete ridges); preventing loss of skin or hair elasticity, for example, due to loss, damage and/or inactivation of functional skin elastin, resulting in such conditions as elastosis, sagging, loss of skin or hair recoil from deformation; reduction in cellulite; change in coloration to the skin, hair, or nails, for example, under-eye circles, blotchiness (e.g., uneven red coloration due to, for example, rosacea), sallowness, discoloration caused by telangiectasia or spider vessels, dryness, brittleness, and graying hair.

IV. Examples

The following describe non-limiting examples of the personal-care composition. The reported percentages indicate the weight of the component expressed as a percentage of the total weight of the personal-care composition. Each Example may comprise one or more of the optional ingredients in amounts as disclosed herein. The Examples may be prepared as follows.

In a suitable vessel, combine the aqueous-phase ingredients and heat to 90° C. with gentle mixing. In a separate vessel, combine the sunscreens (e.g., ethylhexyl salicylate, homosalate, octocrylene, butyl methoxydibenzoylmethane, benzophenone-3), sunscreen solvent (e.g., isopropyl lauroyl sarcosinate), and wax (e.g., Cirebelle 303, Accumelt 72, Accumelt 82, or Accumelt 90) and heat to 90° C. with mixing. When both solutions are translucent and free of particulates to the naked eye, pour the hot water phase into the sunscreen mixture, then immediately add the remaining silicone phase ingredients to the same container. Stir vigorously until smooth and homogeneous while maintaining the temperature of the product above the wax melt point. Remove the product from the heat source and cool to 33° C.

with constant stirring. Scrape the sides of the container frequently to ensure the product is sheared homogeneously. Pour product into suitable containers.

Alternatively, the product can be prepared without shear during cooling. In this case, upon removal from the heat source, the hot emulsion is immediately poured into suitable containers and allowed to come to room temperature.

| Ingredients | Ex. 1 | Ex. 2 | Ex. 3 | Ex. 4 | Ex. 5 |
|---|---|---|---|---|---|
| Silicone Phase | | | | | |
| Ethylhexyl Salicylate | 5.00 | 5.00 | 5.00 | 5.00 | 5.00 |
| Homosalate | 3.50 | 10.00 | 10.00 | 10.00 | 10.00 |
| Octocrylene | 1.30 | 1.30 | 1.70 | 2.60 | 2.60 |
| Butyl Methoxy-dibenzoylmethane | 1.50 | 1.50 | 2.00 | 3.00 | 3.00 |
| Benzophenone-3 | — | — | 2.50 | 4.00 | 4.00 |
| Isopropyl Lauroyl Sarcosinate | 6.00 | 6.00 | 3.00 | 4.00 | 12.00 |
| Dow Corning ™ 9045[1] | 54.00 | 47.55 | 46.05 | 41.65 | 25.75 |
| KSG-310[2] | 3.00 | 3.00 | 3.00 | 3.00 | 3.00 |
| Tospearl ™ 145A[3] | 6.00 | 6.00 | 6.00 | 6.00 | 6.00 |
| Mattewax 511[4] | 4.00 | — | — | — | 4.00 |
| Micropoly 220L[5] | — | 4.00 | 4.00 | 4.00 | — |
| Cab-O-Sil T720[6] | 0.10 | — | — | — | — |
| Dry Flow PC[7] | 1.00 | — | — | — | — |
| Cirebelle 303[8] | — | — | — | — | — |
| Accumelt 72[9] | — | — | — | — | — |
| Accumelt 82[9] | — | — | — | — | — |
| Accumelt 90[9] | 2.00 | 3.00 | 5.00 | 5.00 | 12.00 |
| KF-6105[10] | — | 0.50 | 0.50 | 0.50 | 0.50 |
| KF-6038[11] | 0.50 | — | — | — | — |
| Perfume | 0.25 | 0.15 | 0.25 | 0.25 | 0.15 |
| Aqueous Phase | | | | | |
| Propylene Glycol | 3.20 | 3.20 | 3.20 | 3.20 | 3.20 |
| Purified Water | qs | qs | qs | qs | qs |
| Glycerin | 2.00 | 2.00 | 2.00 | 2.00 | 2.00 |
| White Tea Extract[12] | 1.00 | 1.00 | 1.00 | 1.00 | 1.00 |
| Ginseng[13] | 0.50 | 0.50 | 0.50 | 0.50 | 0.50 |
| Niacinamide | 2.00 | 2.00 | 2.00 | 2.00 | 2.00 |
| Palestrina[14] | 0.58 | 0.58 | 0.58 | 0.58 | 0.58 |
| Panthenol | 0.20 | 0.20 | 0.22 | 0.22 | 0.25 |
| Hexamidine diisethionate | 0.10 | 0.10 | 0.10 | 0.10 | 0.10 |
| Disodium EDTA | 0.01 | 0.01 | 0.01 | 0.01 | 0.01 |
| Total | 100.00 | 100.00 | 100.00 | 100.00 | 100.00 |

| Ingredients | Ex. 6 | Ex. 7 | Ex. 8 | Ex. 9 | Ex. 10 |
|---|---|---|---|---|---|
| Silicone Phase | | | | | |
| Ethylhexyl Salicylate | 4.50 | 4.50 | 4.50 | 4.50 | 4.50 |
| Homosalate | 9.00 | 9.00 | 9.00 | 9.00 | 9.00 |
| Octocrylene | 1.70 | 1.70 | 1.70 | 1.70 | 1.70 |
| Butyl Methoxy-dibenzoylmethane | 3.00 | 3.00 | 2.00 | 2.00 | 2.00 |
| Benzophenone-3 | 4.00 | 4.00 | 2.00 | 2.00 | 2.00 |
| Isopropyl Lauroyl Sarcosinate | 4.00 | 4.00 | 3.00 | 3.00 | 3.00 |
| Dow Corning ™ 9045[1] | 20.50 | — | 47.15 | 47.15 | 47.05 |
| KSG-310[2] | 3.00 | 3.00 | 3.00 | 3.00 | 3.00 |
| Tospearl ™ 145A[3] | 6.00 | 6.00 | 6.00 | 6.00 | 6.00 |
| Mattewax 511[4] | — | — | — | — | — |
| Micropoly 220L[5] | 4.00 | 4.00 | 4.00 | 4.00 | 4.00 |
| Cab-O-Sil T720[6] | — | — | — | — | — |
| Dry Flow PC[7] | — | — | — | — | — |
| Cirebelle 303[8] | — | — | 5.00 | — | — |
| Accumelt 72[9] | — | — | — | 5.00 | — |
| Accumelt 82[9] | — | — | — | — | 5.00 |
| Accumelt 90[9] | 6.00 | 6.00 | — | — | — |
| KF-6105[10] | 0.50 | 0.50 | 0.50 | 0.50 | 0.50 |
| KF-6038[11] | — | — | — | — | — |
| Perfume | 0.25 | 0.25 | 0.15 | 0.15 | 0.15 |
| Aqueous Phase | | | | | |
| Propylene Glycol | 5.00 | 5.00 | 3.20 | 3.20 | 3.20 |
| Purified Water | qs | qs | qs | qs | qs |
| Glycerin | 10.00 | 10.00 | 2.00 | 2.00 | 2.00 |
| White Tea Extract[12] | 1.00 | 1.00 | 1.00 | 1.00 | 1.00 |
| Ginseng[13] | 1.00 | 1.00 | 0.50 | 0.50 | 0.50 |
| Niacinamide | 5.00 | 5.00 | 2.00 | 2.00 | 2.00 |
| Palestrina[14] | 0.58 | 0.58 | 0.58 | 0.58 | 0.58 |
| Panthenol | 0.50 | 0.50 | 0.20 | 0.25 | 0.20 |
| Hexamidine diisethionate | 0.10 | 0.10 | 0.10 | 0.10 | 0.10 |
| Disodium EDTA | 0.01 | 0.01 | 0.01 | 0.01 | 0.01 |
| Total | 100.00 | 100.00 | 100.00 | 100.00 | 100.00 |

[1]Dimethicone Crosspolymer (about 12%) and Cyclopentasiloxane (about 88%) from Dow Corning ™, Midland, MI.
[2]PEG-15/Lauryl Dimethicone Crosspolymer and Mineral Oil from Shin-Etsu ™, Newark, CA.
[3]Polymethylsilsesquioxane from Momentive ™ Performance Materials, Inc., Albany, NY.
[4]Polypropylene from Micro Powders, Inc., Tarrytown, NY.
[5]Polyethylene from Micro Powders, Inc., Tarrytown, NY.
[6]Fumed Silica from Cabot Corp.
[7]Dry-Flo PC from National Starch & Chemical Company, Bridgewater, NJ.
[8]Polyethylene Wax from Arch Chemicals, Inc., South Plainfield, NJ.
[9]Synthetic Wax from The International Group Inc., Toronto, Ontario.
[10]Lauryl Polyglyceryl-3 Polydimethylsiloxyethyl Dimethicone from Shin-Etsu ™, Newark, CA.
[11]Lauryl PEG-9 Polydimethylsiloxyethyl Dimethicone from Shin-Etsu ™, Newark, CA.
[12]White Tea Extract from Carrubba, Inc., Milford, CT.
[13]Ginseng from Symrise, Teterboro, NJ.
[14]Anti-aging peptide solution from Sederma, Inc., Edison, NJ.

V. Comparative Examples

The following is a comparison between examples falling within the present invention and comparative examples using conventional materials. The reported percentages indicate the weight of the component expressed as a percentage of the total weight of the personal-care composition. The Comparative Examples may comprise one or more of the optional ingredients in amounts also disclosed herein. The Comparative Examples may be prepared by the methods used in preparation of the Examples above from the following components. Data shown in these comparative examples was obtained using the former preparation methodology, wherein product is stirred until the product cools to 33° C. Product stability is determined via visual assessment of oil syneresis and through Brookfield viscosity measurements.

To determine oil syneresis, cylindrical containers with the dimensions of 1.5" tall and 2.0" in diameter are filled with approximately 50 g of product. The containers are then placed at 40° C. and room temperature for 5 days. The samples are visually monitored at temperature to determine if liquid synereses from the bulk product, rising to the surface over time. If no syneresis occurs at either temperature, product stability is deemed "stable;" if syneresis occurs at either temperature, product stability is deemed "unstable." For perspective, in cases where product stability is "unstable," the quantity of oil syneresed may be large enough that it can be poured or pipetted from the surface.

Additionally, to assess product stability at high temperature, viscosity measurements are acquired before and after exposure to 40° C. Multiple initial viscosity measurements ($V_i$) for each batch are acquired 24 h after completing the batch on a Brookfield™ RVDV-II+ Viscometer on a Brookfield Helipath Stand equipped with a T-bar spindle rotating at 5 rpm. The viscosity is measured at multiple points as the spindle moves in a downward direction through previously undisturbed product. Viscosity measurements are also taken on undisturbed samples from the same batch that spent 5 days at 40° C., then returned to room temperature 24 h prior to analysis. These viscosity measurements are called $V_t$. Viscosity growth ($V_g$) is the viscosity difference ($V_t - V_i$). To maintain product integrity throughout the product's supply chain and shelf-life, $V_g$ should ideally be ±10,000 cps. In one embodiment, $V_g$ is <50,000 cps, or <25,000 cps, or <10,000 cps.

Comparative Examples 1-3 highlight the oil syneresis advantage gained when a preferred wax is included within a formulation falling within the present invention (E1). The same stability advantage is not attained with equivalent or even elevated levels of non-emulsifying or emulsifying elastomers including a dimethicone crosspolymer (DC9045) (C2 and C3) or a polyglycerol cross-linked elastomer (KSG-310) (C4). C2-C4 fall outside the present invention.

| Ingredients | E1 | C2 | C3 | C4 |
|---|---|---|---|---|
| Silicone Phase | | | | |
| Ethylhexyl Salicylate | 5.00 | 5.00 | 5.00 | 5.00 |
| Homosalate | 10.00 | 10.00 | 10.00 | 10.00 |
| Octocrylene | 2.60 | 2.60 | 2.60 | 2.60 |
| Butyl Methoxydibenzoylmethane | 3.00 | 3.00 | 3.00 | 3.00 |
| Benzophenone-3 | 4.00 | 4.00 | 4.00 | 4.00 |
| Isopropyl Lauroyl Sarcosinate | 4.00 | 4.00 | 4.00 | 4.00 |
| Dow Corning ™ 9045[1] | 40.75 | 45.75 | 55.75 | 40.75 |
| KSG-310[2] | 3.00 | 3.00 | 3.00 | 8.00 |
| Tospearl ™ 145A[3] | 6.00 | 6.00 | — | 6.00 |
| Micropoly 220L[4] | 4.00 | 4.00 | — | 4.00 |
| Accumelt 90[5] | 5.00 | — | — | — |
| KF-6105[6] | 0.50 | 0.50 | 0.50 | 0.50 |
| Perfume | 0.15 | 0.15 | 0.15 | 0.15 |
| Aqueous Phase | | | | |
| Propylene Glycol | 3.20 | 3.20 | 3.20 | 3.20 |
| Purified Water | qs | qs | qs | qs |
| Glycerin | 2.00 | 2.00 | 2.00 | 2.00 |
| White Tea Extract[7] | 1.00 | 1.00 | 1.00 | 1.00 |
| Ginseng[8] | 0.50 | 0.50 | 0.50 | 0.50 |
| Niacinamide | 2.00 | 2.00 | 2.00 | 2.00 |
| Palestrina[9] | 0.58 | 0.58 | 0.58 | 0.58 |
| Panthenol | 0.25 | 0.25 | 0.25 | 0.25 |
| Hexamidine diisethionate | 0.10 | 0.10 | 0.10 | 0.10 |
| Disodium EDTA | 0.01 | 0.01 | 0.01 | 0.01 |
| Total | 100.00 | 100.00 | 100.00 | 100.00 |
| Oil Syneresis | Stable | Unstable | Unstable | Unstable |

[1] Dimethicone Crosspolymer (about 12%) and Cyclopentasiloxane (about 88%) from Dow Corning ™, Midland, MI.
[2] PEG-15/Lauryl Dimethicone Crosspolymer and Mineral Oil from Shin-Etsu ™, Newark, CA.
[3] Polymethylsilsesquioxane from Momentive ™ Performance Materials, Inc., Albany, NY.
[4] Polyethylene from Micro Powders, Inc., Tarrytown, NY.
[5] Synthetic Polymethylene Wax from The International Group Inc., Toronto, Ontario.
[6] Lauryl Polyglyceryl-3 Polydimethylsiloxyethyl Dimethicone from Shin-Etsu ™, Newark, CA.
[7] White Tea Extract from Carrubba, Inc., Milford, CT.
[8] Ginseng from Symrise, Teterboro, NJ.
[9] Anti-aging peptide solution from Sederma, Inc., Edison, NJ.

Comparative Examples 5-8 demonstrate the formula flexibility gained when a small amount of a preferred hydrocarbon wax is included within the formulation (E5 and E6, falling within the present invention). This flexibility is demonstrated by accommodating higher levels of aqueous phase and polar oils while maintaining good product stability. The same advantage is not attained with equivalent or elevated levels of non-emulsifying or emulsifying elastomers including a dimethicone crosspolymer (DC9045) (C7) or a polyglycerol cross-linked elastomer (KSG-310) (C8). C7-C8 fall outside the present invention.

| Ingredients | E5 | E6 | C7 | C8 |
|---|---|---|---|---|
| Silicone Phase | | | | |
| Ethylhexyl Salicylate | 4.50 | 4.50 | 4.50 | 4.50 |
| Homosalate | 9.00 | 9.00 | 9.00 | 9.00 |
| Octocrylene | 2.60 | 2.60 | 2.60 | 2.60 |
| Butyl Methoxydibenzoylmethane | 3.00 | 3.00 | 3.00 | 3.00 |
| Benzophenone-3 | 4.00 | 4.00 | 4.00 | 4.00 |
| Isopropyl Lauroyl Sarcosinate | 4.00 | 4.00 | 4.00 | 4.00 |
| Dow Corning ™ 9045[1] | 19.60 | — | 6.00 | — |
| KSG-310[2] | 3.00 | 3.00 | 3.00 | 9.00 |
| Tospearl ™ 145A[3] | 6.00 | 6.00 | 6.00 | 6.00 |
| Micropoly 220L[4] | 4.00 | 4.00 | 4.00 | 4.00 |
| Accumelt 90[5] | 6.00 | 6.00 | — | — |
| KF-6105[6] | 0.50 | 0.50 | 0.50 | 0.50 |
| Perfume | 0.25 | 0.25 | 0.25 | 0.25 |
| Aqueous Phase | | | | |
| Propylene Glycol | 5.00 | 5.00 | 5.00 | 5.00 |
| Purified Water | qs | qs | qs | qs |
| Glycerin | 10.00 | 10.00 | 10.00 | 10.00 |
| White Tea Extract[7] | 1.00 | 1.00 | 1.00 | 1.00 |
| Ginseng[8] | 1.00 | 1.00 | 1.00 | 1.00 |
| Niacinamide | 5.00 | 5.00 | 5.00 | 5.00 |
| Palestrina[9] | 0.58 | 0.58 | 0.58 | 0.58 |
| Panthenol | 0.50 | 0.50 | 0.50 | 0.50 |
| Hexamidine diisethionate | 0.10 | 0.10 | 0.10 | 0.10 |
| Disodium EDTA | 0.01 | 0.01 | 0.01 | 0.01 |
| Total | 100.00 | 100.00 | 100.00 | 100.00 |
| Oil Syneresis | Stable | Stable | Unstable | Unstable |

[1] Dimethicone Crosspolymer (about 12%) and Cyclopentasiloxane (about 88%) from Dow Corning ™, Midland, MI.
[2] PEG-15/Lauryl Dimethicone Crosspolymer and Mineral Oil from Shin-Etsu ™, Newark, CA.
[3] Polymethylsilsesquioxane from Momentive ™ Performance Materials, Inc., Albany, NY.
[4] Polyethylene from Micro Powders, Inc., Tarrytown, NY.
[5] Synthetic Polymethylene Wax from The International Group Inc., Toronto, Ontario.
[6] Lauryl Polyglyceryl-3 Polydimethylsiloxyethyl Dimethicone from Shin-Etsu ™, Newark, CA.
[7] White Tea Extract from Carrubba, Inc., Milford, CT.
[8] Ginseng from Symrise, Teterboro, NJ.
[9] Anti-aging peptide solution from Sederma, Inc., Edison, NJ.

Comparative Examples 9-12 demonstrate the unique stability advantages attained when a small amount of a preferred hydrocarbon wax is included within the formulation (E9, falling within the present invention). The same advantage is not attained with waxes outside the preferred specifications, such as a fatty alcohol wax (behenyl alcohol) (C10), fatty ester wax (stearyl behenate) (C11), or a highly branched hydrocarbon micro crystalline wax (Microcrystalline Wax SP-96) (C12). These comparative examples exhibit instabilities in the form of syneresis and a viscosity growth after 5 days at 40° C. C10-C12 fall outside the present invention.

| Ingredients | E9 | C10 | C11 | C12 |
|---|---|---|---|---|
| Silicone Phase | | | | |
| Ethylhexyl Salicylate | 5.00 | 5.00 | 5.00 | 5.00 |
| Homosalate | 10.00 | 10.00 | 10.00 | 10.00 |
| Octocrylene | 1.70 | 1.70 | 1.70 | 1.70 |
| Butyl Methoxydibenzoylmethane | 3.00 | 3.00 | 3.00 | 3.00 |
| Benzophenone-3 | 4.00 | 4.00 | 4.00 | 4.00 |
| Isopropyl Lauroyl Sarcosinate | 4.00 | 4.00 | 4.00 | 4.00 |
| Dow Corning ™ 9045[1] | 40.75 | 40.75 | 40.75 | 40.75 |
| KSG-310[2] | 3.00 | 3.00 | 3.00 | 3.00 |
| Tospearl ™ 145A[3] | 6.00 | 6.00 | 6.00 | 6.00 |
| Micropoly 220L[4] | 4.00 | 4.00 | 4.00 | 4.00 |
| Accumelt 90[5] | 5.00 | — | — | — |
| Behenyl Alcohol | — | 5.00 | — | — |
| Stearyl Behenate | — | — | 5.00 | — |
| Microcrystalline Wax SP-96[6] | — | — | — | 5.00 |

-continued

| Ingredients | E9 | C10 | C11 | C12 |
|---|---|---|---|---|
| KF-6105[7] | 0.50 | 0.50 | 0.50 | 0.50 |
| Perfume | 0.15 | 0.15 | 0.15 | 0.15 |
| Aqueous Phase | | | | |
| Propylene Glycol | 3.20 | 3.20 | 3.20 | 3.20 |
| Purified Water | qs | qs | qs | qs |
| Glycerin | 2.00 | 2.00 | 2.00 | 2.00 |
| White Tea Extract[8] | 1.00 | 1.00 | 1.00 | 1.00 |
| Ginseng[9] | 0.50 | 0.50 | 0.50 | 0.50 |
| Niacinamide | 2.00 | 2.00 | 2.00 | 2.00 |
| Palestrina[10] | 0.58 | 0.58 | 0.58 | 0.58 |
| Panthenol | 0.25 | 0.25 | 0.25 | 0.25 |
| Hexamidine diisethionate | 0.10 | 0.10 | 0.10 | 0.10 |
| Disodium EDTA | 0.01 | 0.01 | 0.01 | 0.01 |
| Total | 100.00 | 100.00 | 100.00 | 100.00 |
| Oil Syneresis | Stable | Unstable | Unstable | Unstable |
| Viscosity Growth ($V_g$) after 5 days at 40° C. (cps) | 8,000 | 20,000 | 40,000 | 60,000 |

[1]Dimethicone Crosspolymer (about 12%) and Cyclopentasiloxane (about 88%) from Dow Corning ™, Midland, MI.
[2]PEG-15/Lauryl Dimethicone Crosspolymer and Mineral Oil from Shin-Etsu ™, Newark, CA.
[3]Polymethylsilsesquioxane from Momentive ™ Performance Materials, Inc., Albany, NY.
[4]Polyethylene from Micro Powders, Inc., Tarrytown, NY.
[5]Synthetic Wax from The International Group Inc., Toronto, Ontario.
[6]Microcrystalline Wax from Strahl & Pitsch.
[7]Lauryl Polyglyceryl-3 Polydimethylsiloxyethyl Dimethicone from Shin-Etsu ™, Newark, CA.
[8]White Tea Extract from Carrubba, Inc., Milford, CT.
[9]Ginseng from Symrise, Teterboro, NJ.
[10]Anti-aging peptide solution from Sederma, Inc., Edison, NJ.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A stable personal-care composition in the form of a water-in-oil emulsion comprising:
   a) from about 0.01% to about 10% of a hydrocarbon wax which is straight chain wax saturated to greater than 90%, wherein at least some of the wax forms discrete wax crystals within the oil phase;
   b) greater than 10% of a polar oil; and
   c) from about 1% to about 8% of a non-emulsifying silicone elastomer;
   wherein the weight ratio of wax to polar oil is from about 0.01 to about 0.5, wherein the personal care composition is not in the form of a solid, and wherein the personal care composition comprises a viscosity growth ($V_g$) less than 25,000 cps.

2. The stable personal-care composition of claim 1, wherein the hydrocarbon wax is selected from the group consisting of polyethylenes, polymethylenes, and combinations thereof.

3. The stable personal-care composition of claim 1, wherein the hydrocarbon wax comprises from 20 to 100 carbon atoms.

4. The stable personal-care composition of claim 1, wherein the hydrocarbon wax comprises an alkyne:alkene carbon ratio lower than about 0.05.

5. The stable personal-care composition of claim 1, wherein the hydrocarbon wax comprises a polydispersity index less than about 1.1.

6. The stable personal-care composition of claim 1, wherein the hydrocarbon wax comprises a melt point of from about 55 degrees to about 150 degrees C.

7. The stable personal-care composition of claim 1, wherein the polar oil comprises a sunscreen.

8. The stable personal-care composition of claim 7, wherein the sunscreen is selected from the group consisting of benzophenone-3, bis-ethylhexyloxyphenol methoxyphenyl triazine, butyl methoxydibenzoylmethane, diethylamino hydroxy-benzoyl hexyl benzoate, ethylhexyl methoxy-cinnamate, ethylhexyl salicylate, ethylhexyl triazone, octocrylene, homosalate, polysilicone-15, and mixtures thereof.

9. The stable personal-care composition of claim 1, wherein the polar oil is selected from the group consisting of butyl phthalimide, isopropyl phthalimide, phenylethyl benzoate, dicaprylyl carbonate, isopropyl lauroyl sarcosinate, butyl octylsalicylate, dioctyl malate, dicaprylyl maleate, di-isopropyl adipate, isononyl isononanoate, isopropyl isostearate, propylene glycol dicaprate, C12-15 alcohol benzoate, derivatives, and mixtures thereof.

10. The stable personal-care composition of claim 1, wherein the polar oil comprises:
   a) a sunscreen selected from the group consisting of benzophenone-3, bis-ethylhexyloxyphenol methoxyphenyl triazine, butyl methoxydibenzoyl-methane, diethylamino hydroxy-benzoyl hexyl benzoate, ethylhexyl methoxy-cinnamate, ethylhexyl salicylate, ethylhexyl triazone, octocrylene, homosalate, polysilicone-15, and mixtures thereof; and
   b) a member selected from the group consisting of butyl phthalimide, isopropyl phthalimide, phenylethyl benzoate, dicaprylyl carbonate, isopropyl lauroyl sarcosinate, butyl octylsalicylate, dioctyl malate, dicaprylyl maleate, di-isopropyl adipate, isononyl isononanoate, isopropyl isostearate, propylene glycol dicaprate, C12-15 alcohol benzoate, derivatives, and mixtures thereof.

11. The stable personal-care composition of claim 1, further comprising a skin-care active, wherein the skin-care active is selected from the group consisting of vitamins, peptides, sugar amines, oil control agents, tanning actives, anti-acne actives, desquamation actives, anti-cellulite actives, chelating agents, skin lightening agents, flavonoids, protease inhibitors, non-vitamin antioxidants and radical scavengers, hair growth regulators, anti-wrinkle actives, anti-atrophy actives, minerals, phytosterols and/or plant hormones, tyrosinase inhibitors, anti-inflammatory agents, N-acyl amino acid compounds, antimicrobials, antifungals, and mixtures thereof.

12. The stable personal-care composition of claim 1, further comprising a skin-care active, wherein the skin-care active is selected from the group consisting of a vitamin $B_3$ compound, a sugar amine, a peptide, a hexamidine compound, and combinations thereof.

13. The stable personal-care composition of claim 1, further comprising a particulate material.

* * * * *